United States Patent [19]

Robinson et al.

[11] 4,295,252
[45] Oct. 20, 1981

[54] METHOD FOR MEASURING YARN SHRINKAGE AND CRIMP DEVELOPMENT

[75] Inventors: Bruce A. Robinson, Gananoque; John R. Thompson, Yarker, both of Canada

[73] Assignee: E. I. Du Pont de Nemours & Co., Wilmington, Del.

[21] Appl. No.: 158,609

[22] Filed: Jun. 11, 1980

Related U.S. Application Data

[63] Continuation-in-part of Ser. No. 56,947, Jul. 12, 1979, abandoned.

[51] Int. Cl.³ .......................... D02G 1/20; D02J 1/12
[52] U.S. Cl. ...................................... 28/248; 28/281; 73/160
[58] Field of Search .................. 73/160; 226/42, 44; 28/248, 281; 19/66.1

[56] References Cited

U.S. PATENT DOCUMENTS

| | | | |
|---|---|---|---|
| 2,744,408 | 5/1956 | Seney | 73/580 |
| 3,047,198 | 7/1962 | Long | 226/42 |
| 3,333,467 | 8/1967 | Hoskins | 73/160 |
| 3,492,838 | 2/1970 | Reiners et al. | 68/5 |
| 3,694,634 | 9/1972 | Horst et al. | 226/42 X |
| 3,721,376 | 3/1973 | Christian et al. | 226/42 |
| 3,726,137 | 4/1973 | Denton | 28/248 X |
| 3,762,220 | 10/1973 | Gusack et al. | 73/160 |
| 3,763,669 | 10/1973 | Bous et al. | 57/157 TS |
| 4,035,880 | 7/1977 | Hills et al. | 28/248 X |

OTHER PUBLICATIONS

Publication–"*Testing Method for Measurement of Crimp ... in Yarns*", by Lünenschloss et al., Ref.–Chemiefasern 21 4-49 (1971) Jan., pp. 11–12.

Publication–"*Controlling Textured Yarn by Measurement of Reactive Force*", by M. J. Denton, Shirly Institute Part 2, Appendix II (4 pages), Textile Month 3/1973, pp. 30–31.

Publication–Research Disclosure Journal, Apr. 1974, "*Crimp Characterization Instrument*", 3 pages.

*Primary Examiner*—Daniel M. Yasich

[57] ABSTRACT

A method for measuring continuously shrinkage and crimp development in a long continuous sample of yarn involves the steps providing a zero-tension loop, applying a standard tension, then developing crimp in a single downward pass through a hot air chamber providing a second zero-tension loop and thereafter retensioning it. The shrinkage and crimp development is calculated from differential speeds of rolls advancing the yarn.

1 Claim, 1 Drawing Figure

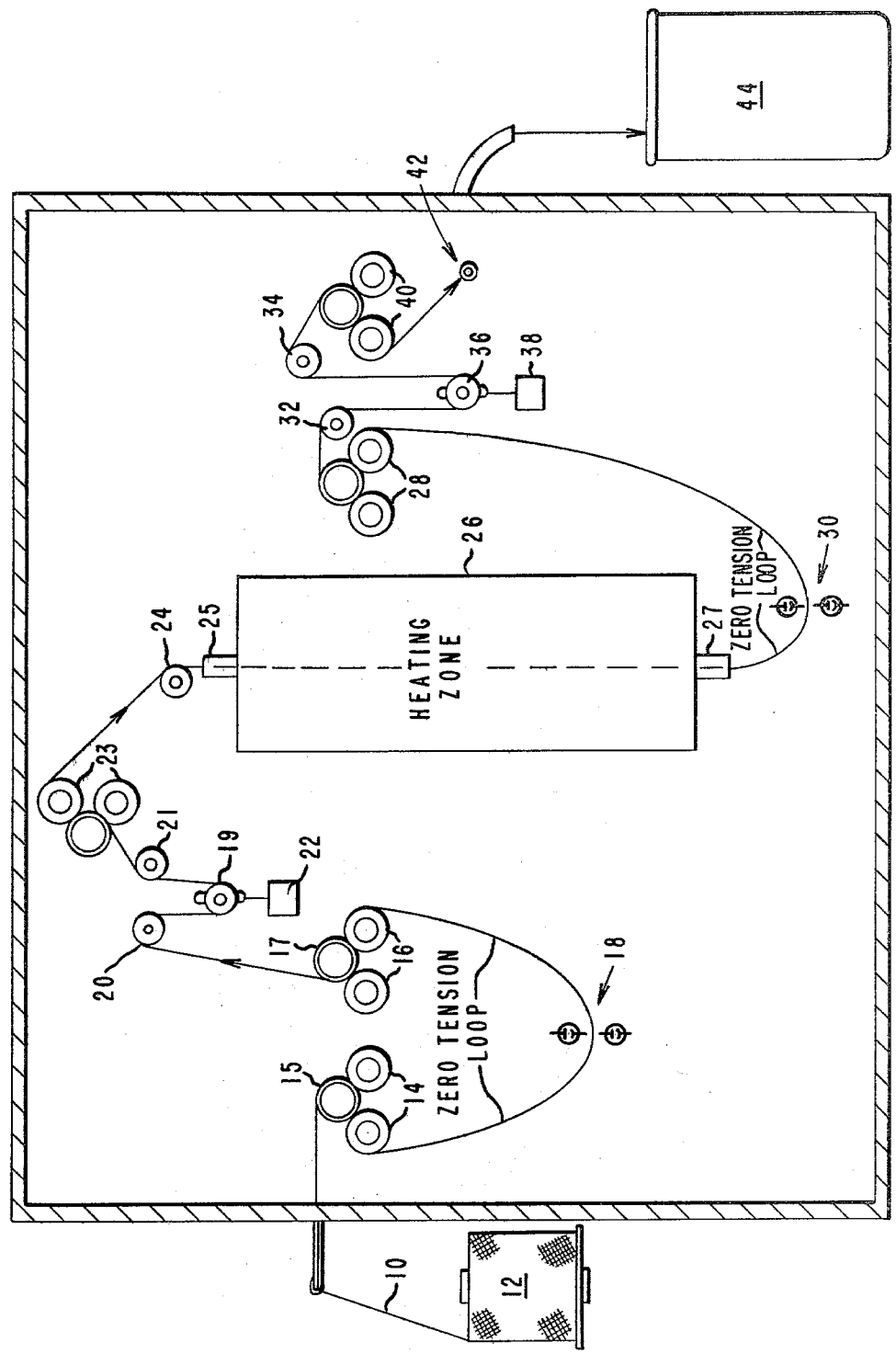

METHOD FOR MEASURING YARN SHRINKAGE AND CRIMP DEVELOPMENT

CROSS REFERENCES TO RELATED APPLICATION

This application is a continuation-in-part of our prior U.S. application Ser. No. 56,947, filed July 12, 1979, now abandoned.

TECHNICAL FIELD

This invention concerns a method for measuring continuously shrinkage and crimp development of a running yarn sample.

BACKGROUND OF THE INVENTION

Automatic instruments for measuring certain properties of yarns automatically on the run are known. However, properties such as shrinkage and crimp development in yarns which develop crimp upon heating at low tension are quite sensitive to the tension under which such crimp is developed and measured. A considerable amount of the shrinkage or crimp development in such yarns becomes evident only at very low tensions, such as are encountered in a pile carpet when the fabric is dyed at elevated temperature where the pile yarn may be under zero tension while being agitated in the dye bath. The conventional method of forming skeins and measuring their length before and after crimp development during zero-tension tumbling allows for full retraction, but this method is not continuous or automatic Automatic instruments used for measuring shrinkage or crimp development in such yarns, such as described by M. J. Denton in U.S. Pat. No. 3,726,137 and by Lunenschloss et al. in Chemiefasern 21, 41–49 (1971) Jan., have kept the yarn under controlled low tension during heating and measuring of properties. In such cases the yarn is unable to develop the same amount of shrinkage or crimp which the yarn undergoes in normal fabric processing, and therefore the measurement does not reflect conditions of actual use. Variations in yarn properties which may cause undesirable appearance, such as configurational dye streaks in fabrics, thus may not be detected when such properties are measured with an instrument which maintains substantial tension on the yarn. This is particularly true of yarns which have a low degree of shrinkage or crimp and which are desired for high-luster fabrics.

The traditional way of beginning a measurement is to place the yarn under a standard tension using one of a variety of known tensioning devices, as described for example in U.S. Pat. Nos. 3,726,137 to Denton and 3,762,220 to Gusack. However, such tensioners are usually affected by variations in tension caused by varying drag on the yarn as it comes off a package, tension being low when the yarn is feeding from the near end of the package and higher as it feeds from the farther end. Yarn defects may cause tension plucks as yarn slides over them. Such tension variations may be magnified by conventional tensioning systems, or at least are not eliminated by them.

SUMMARY OF THE INVENTION

An improved method of measurement of yarn shrinkage and crimp development has now been developed to obtain reliable bulk and other useful yarn data which permits use of long continuous sample length at increased yarn speed with excellent precision. The method involves the steps of advancing the yarn from a source through a tension zone, a heating zone and an elongation zone in a system that regulates the speed of the rolls advancing the yarn through the above-mentioned zones. Property measurements are determined from the ratio of roll speeds as will be detailed later. The improvement involves maintaining the yarn in a zero-tension zone by means of a free-hanging loop as it passes from the source to the tension zone and passing the yarn downward through the heating zone into another zero-tension zone by means of a second-free hanging loop prior to entering the elongation zone.

BRIEF DESCRIPTION OF THE DRAWING

The drawing is a schematic diagram of the method of this invention.

DETAILED DESCRIPTION OF THE PREFERRED EMBODIMENT

Referring to the drawing, yarn 10 is taken from package 12 by driven rolls 14 with associated nip roll 15 to prevent slippage of the yarn. Yarn 10 then passes downward in a free-hanging loop and up to driven rolls 16 with associated nip roll 17. Rolls 16 are driven at constant speed, and the length of the loop between rolls 14 and 16 is controlled by a noncontacting control system 18 such as photoelectric cells to sense the position of the loop, which in turn controls the speed of rolls 14 to maintain the length of the loop between an upper and lower limit. The yarn then passes to the first tension zone over pulleys 20 and 21 having low friction bearings, between which is positioned tensioner pully 19 hanging on the loop of yarn and having weight 22 to provide a standardized tension such as 0.1 grams per denier. Different values of weight 22 are provided for different deniers of yarn. An optical system (not shown) senses the position of pulley 19 and controls the speed of roll 23 to maintain pulley 19 at the desired position. Yarn 10 then passes over free-running roll 24 and enters heating zone chamber 26 supplied with hot air (from a source not illustrated) at accurately regulated temperature and flow rate. As the yarn passes downward through heating chamber 26, hot air flows outwardly through both yarn entrance 25 and yarn exit 27 to prevent ambient air from entering the chamber. The flow rate of the hot air is adjusted to maintain a slight tension on the yarn within chamber 26 due to fluid drag as the hot air exits. This outward flow also removes the cold air which is entrained with the yarn entering at entrance 25 and prevents ambient air from entering upward at exit 27 through convection. Yarn 10 leaving exit 27 proceeds downward in a second free-hanging loop then upward to driven rolls 28 which are controlled by a noncontacting device 30, for example photoelectric cells, to maintain the loop length within an upper and lower limit. The yarn cools to approximately ambient temperature during its travel from exit 27 to rolls 28. Yarn 10 then passes to the second tension zone over free-running pulleys 32 and 34 between which is positioned tensioner pulley 36 with weight 38, the position of which is controlled by a measuring system (not shown) which senses the position of pulley 36 and controls the speed of rolls 40 in the elongation zone. Yarn 10 then enters aspirator 42 which deposits it in a waste container such as 44.

The free-hanging loop between rolls 14 and 16 isolates the measuring system from tension differences due to removing yarn from package 12. This also eliminates any elasticity effects so that the tension applied by tensioner pulley 19 and weight 22 will provide a more accurate base for measuring subsequent behavior of the yarn. The heating of the yarn in chamber 26 takes place under only the weight of the yarn loop and the slight drag produced by the outflowing hot air, but this yarn is then able to retract completely while still hot as it leaves exit 27 and approaches zero tension at the bottom of the second free-hanging loop where even the effect of its own weight is minimized.

The speeds of rolls 16, 23, 28 and 40 are obtained by photoelectric devices which count the teeth of a gear attached to each roll shaft. These pulses are fed into a computer which calculates one or more properties and displays the results on a panel and/or prints the results through a teletype or similar devices (not shown). Three typical measurements which may be made are:

$$\% \text{ Bulk Crimp Elongation} = \frac{(\text{speed of rolls 40}) - (\text{speed of rolls 28})}{(\text{speed of rolls 28})} \times 100 \quad (1)$$

$$\% \text{ Residual Crimp Elongation} = \frac{(\text{speed of rolls 23}) - (\text{speed of rolls 16})}{(\text{speed of rolls 16})} \times 100 \quad (2)$$

$$\% \text{ Fiber Shrinkage} = \frac{(\text{speed of rolls 23}) - (\text{speed of rolls 40})}{(\text{speed of rolls 23})} \times 100 \quad (3)$$

For most purposes the measurement reported is the average value for a preset length of sample. However, the computer may also be programmed to report variations of a property within the given sample length.

The hot air within heating chamber 26 is preferably dry because the addition of moisture in the form of steam is more difficult to control accurately and may cause condensation problems outside the chamber. The flow rate of hot air through and out of heating chamber 26 should be no less than that required to maintain an outward flow of hot air at both yarn entrance 25 and yarn exit 27. Higher flows may be desirable for opening large yarn bundles to thoroughly heat all filaments and provide sufficient agitation for all filaments to develop crimp. However, high flow rates also impose more tension on the yarn during the heating process. Flow rates should not exceed a value which reduces the measured crimp elongation and shrinkage significantly.

The various zero-tension and high-tension zones in the process both before and after bulking can accommodate additional detecting devices to measure luster, denier, denier uniformity, initial modulus and so forth.

The improved process of the invention is able to measure crimp and shrinkage parameters over the full range of commercial interest including the low values which are most difficult. The faster analysis time means that more or longer samples may be measured to give more accurate averages or alternately that variations along the end of a yarn may be determined quickly.

The measurement error of the present process has been found to be only about 10 to 15% of the total variance compared to 60–70% measurement error for the skein method.

We claim:
1. In a method for measuring continuously shrinkage and crimp development in yarns which develop crimp upon heating under low tension and wherein the yarn is advanced by driven rolls from a yarn source to a first tension zone, through a heating zone to a second tension zone and then through an elongation zone, whereby shrinkage and crimp development are determined in a measuring system from ratios of driven roll speeds; the improvement comprising: advancing said yarn downwardly in a free-hanging loop as it passes from said source to said first tension zone while maintaining zero tension in the yarn of said loop by noncontacting means sensing the length of the free-hanging loop and in turn controlling the speed of the driven rolls near the yarn source whereby tension differences in the yarn due to removing the yarn from the source are isolated from the measuring system, passing the yarn downward through said heating zone into a second free-hanging loop while maintaining zero tension in the yarn in said second loop by a second noncontacting means sensing the length of the second free-hanging loop and in turn controlling the speed of driven rolls in the second tension zone whereby the yarn is able to retract completely prior to entering the elongation zone, and cooling the yarn while passing upward to the second tension zone.

* * * * *

UNITED STATES PATENT AND TRADEMARK OFFICE
CERTIFICATE OF CORRECTION

PATENT NO. : 4,295,252
DATED : OCTOBER 20, 1981
INVENTOR(S) : BRUCE A. ROBINSON and JOHN R. THOMPSON It is certified that error appears in the above—identified patent and that said Letters Patent is hereby corrected as shown below:

On the printed face sheet of the patent the Assignee reading "E. I. Du Pont de Nemours & Co., Wilmington, Del."

should read

--Du Pont Canada Inc., Montreal, Canada--.

Signed and Sealed this

Twenty-sixth Day of January 1982

[SEAL]

Attest:

*Attesting Officer*

GERALD J. MOSSINGHOFF

*Commissioner of Patents and Trademarks*